United States Patent [19]

Schwinn

[11] Patent Number: 5,328,694
[45] Date of Patent: Jul. 12, 1994

[54] STABLE INJECTABLE SOLUTION OF FACTOR VIII

[75] Inventor: Horst Schwinn, Marburg, Fed. Rep. of Germany

[73] Assignee: Octapharma AG, Glarus, Switzerland

[21] Appl. No.: 916,644

[22] Filed: Jul. 20, 1992

[30] Foreign Application Priority Data

Jan. 19, 1990 [DE] Fed. Rep. of Germany ....... 4001451

[51] Int. Cl.$^5$ ..................... A61K 35/14; A61K 37/04; A61K 31/715; C07K 3/02
[52] U.S. Cl. .................................. 424/423; 530/383; 514/53
[58] Field of Search ..................... 530/383; 424/423; 514/53

[56] References Cited

U.S. PATENT DOCUMENTS 4,847,362 7/1989 Mathews et al. .................... 530/383

FOREIGN PATENT DOCUMENTS

| 0035204 | 9/1981 | European Pat. Off. . |
| 0077870 | 5/1983 | European Pat. Off. . |
| 0117064 | 8/1984 | European Pat. Off. . |
| 0314095 | 5/1989 | European Pat. Off. . |
| 0411810 | 2/1991 | European Pat. Off. ............ 530/383 |
| 0112630 | 6/1984 | Japan .................................. 530/383 |
| 8303871 | 11/1982 | World Int. Prop. O. . |

Primary Examiner—Thurman K. Page
Assistant Examiner—Carlos Azpuru
Attorney, Agent, or Firm—Wegner, Cantor, Mueller & Player

[57] ABSTRACT

A stable, injectable solution containing factor VIII suitable for the treatment of humans, natural or synthetic disaccharides, preferably saccharose, in concentrations of from 0.1 to 0.65 mol/l, and one or more amino acids in concentrations of from 0.1 to 1.0 mol/l. A process for preparing same and the use of natural or synthetic disaccharides, preferably saccharose, and one or more amino acids for stabilizing factor VIII.

14 Claims, No Drawings

STABLE INJECTABLE SOLUTION OF FACTOR VIII this application is a continuation-in-part under 35 USC section 120 and section 365 of PCT application No PCT/EP90/02238, filed Dec. 19, 1990.

The present application is directed to a stable injectable solution of factor VIII, a process for the preparation of same, and a use.

Factor VIII is a coagulation factor in the human blood coagulation system involved in blood coagulation and fibrinolysis. Factor VIII is involved in the formation of the plasma prothrombin activator in the endogenic coagulation system.

Deficiency in antihemophilic factor VIII results in pathological disorders of the blood coagulation system in the form of hemophilia. Here, the remaining coagulation factor activity may drop as low as a few percent. For therapy of hemophilia in the case of factor VIII deficiency, coagulation-promoting plasma concentrates such as a cryoprecipitate are used.

However, when using this coagulation factor as a therapeutic agent, it must be noted that it is unstable and may contain fibrinogen and undesired viruses.

Therefore, it is necessary to subject the concentrated coagulation factor to a purification and stabilization process.

In European patent application 88 118 478.2, there is suggested a process for preparing a highly pure, non-infectious antihemophilia factor. Here, the fraction enriched in factor VIII is recovered by gel permeation chromatography using ion exchange materials. Subsequently, work-up of this fraction is likewise effected by a gel permeation chromatography process based on ion exchangers.

European patent application 0,018,561 describes a process for stabilizing blood coagulation factors, particularly factors II, VIII, XIII, and III, as well as plasminogen by heating to from 60° to 70° C. in the presence of glycine and a saccharide at a pH value of between 6.5 and 8, the heating being effected in the presence of saccharose at a concentration of from 20 to 60% by weight and glycine at a concentration of from 1.0 to 3.0 mol/1.

Subsequent to purification and stabilization, the thus obtained concentrate enriched in coagulation factors is sterile-filtered and/or lyophilized. Lyophilized factor VIII preparations are already commercially available.

By adding large amounts of saccharose in stabilizing the enriched concentrates according to prior art, a highly viscous and hence, difficultly filterable protein solution is formed which, however, must be filtered in sterile fashion prior to therapeutic application. For this reason, the concentrates hitherto had to be freed from stabilizer substances prior to sterile filtration. However, such treatment is associated with great technical expense and loss of concentrate.

Due to low stability in solution, antihemophilia factors so far are available as lyophilized preparations only. However, lyophilization is an expensive and energy-consuming production process.

Moreover, lyophilized preparations must be taken up into suitable solvents prior to use. For the user, this represents an inconvenient preparation for therapy.

Therefore, it is an object of the invention to provide factor VIII in a stable, injectable form which is more easily usable and more simple to prepare.

This problem is solved by a stable, injectable solution containing factor VIII preparation suitable for the treatment of humans, natural or synthetic disaccharides, preferably saccharose, in concentrations of from 0.1 to 0.65 mol/1 and one or more amino acids in concentrations of from 0.1 to 1.0 mol/1.

As the amino acid, lysine and/or glycine may be used.

In a special embodiment, the stable, injectable solution contains $Ca^{2+}$ ions or $Cl^-$ ions. The concentration of $Cl^-$ ions preferably is from 0.03 to 0.3 mol/1.

In a particularly preferred embodiment, there is contained saccharose at a concentration of from 0.4 to 0.65 mol/1.

Another object of the invention is a process for preparing a stable, injectable solution, wherein factor VIII preparation suitable for the treatment of humans, a disaccharide in a concentration of from 0.1 to 0.65 mol/1, preferably 0.4 to 0.65 mol/1 of saccharose, and one or more amino acids at concentrations of from 0.1 to 1.0 mol/1 are dissolved in water, sterile-filtered, and filled into ampoules.

Here, as the amino acids, lysine and glycine may be used. Additionally, $Ca^{2+}$ ions or $Cl^-$ ions may be added.

These ready-for-use ampoules, wherein saccharose and one or more amino acids are used for stabilizing factor VIII, can be maintained stable for several weeks at from 0° to 10° C., preferably 4° C. Furthermore, they have the advantage that the plasma fractions enriched in coagulation factor VIII contain saccharose in considerably lower concentrations than usual hitherto in prior art. Thus, the protein solutions resulting therefrom are low in viscosity and more easily filterable than the highly viscous solutions stabilized according to prior art of EP 0,018,561.

The following examples demonstrate typical embodiments of the invention and of the process for preparing a stable, injectable solution of factor VIII.

COMPARATIVE EXAMPLE 1 1

Stabilization of a Factor VIII Concentrate

A solution containing factor VIII is produced according to EP-A 88 108 458.6 or EP-A 88 118 478.2, which are hereby incorporated by reference.

To the collected fractions containing factor VIII is added 0.9 mol/1 of saccharose, 0.25 mol/1 of glycine, 0.25 mol/1 of lysine, and 0,003 mol/1 of $CaCl_2$, followed by sterile filtration.

The solution is stored at from 4° to 8° C. As shown in the following table, factor VIII activity, as compared to a nonstabilized control solution, remains unchanged for weeks.

| Weeks | 0 | 1 | 2 | 5 | 10 | 13 |
|---|---|---|---|---|---|---|
| Factor VIII I.U./ml, control solution | 22 | 20 | 11 | — | — | — |
| Factor VIII I.U./ml, stabilized solution | 22 | 22 | 23 | 21 | 23 | 22 |

COMPARATIVE EXAMPLE 2

Stabilization of a Lyophilized Factor VIII Concentrate Subsequent to Redissolving A factor VIII concentrate is produced as in 1 and lyophilized. Subsequently, the lyophilizate is redissolved in an aqueous solution having the following composition, and filtered in sterile fashion:

0.7 mol/l of saccharose
0.5 mol/l of glycine
0.005 mol/l of $CaCl_2$

The sterile solution is stable at from 4° to 8° C. as shown in Example 1.

What is claimed is:

1. A stable, injectable solution, characterized in that it contains factor VIII suitable for the treatment of hemophilia in humans in need there natural or synthetic disaccharides in a concentration of from 0.1 to 0.65 mol/l and one or more amino acids in concentrations of from 0.1 to 1.0 mol/l.

2. The stable, injectable solution according to claim 1, characterized in that it contains lysine as the amino acid.

3. The stable, injectable solution according to claim 1, characterized in that it contains glycine as the amino acid.

4. The stable, injectable solution according to claim 1, characterized in that it contains, in addition, $Ca^{2+}$ ions or $Cl^-$ ions.

5. The stable, injectable solution according to claim 2, characterized in that it contains, in addition, $Ca^{2+}$ ions or $Cl^-$ ions.

6. The stable, injectable solution according to claim 3, characterized in that it contains, in addition, $Ca^{2+}$ ions or $Cl^-$ ions.

7. The stable, injectable solution according to claim 1, characterized in that saccharose is used as the disaccharide.

8. The stable, injectable solution according to claim 2, characterized in that saccharose is used as the disaccharide.

9. The stable, injectable solution according to claim 3, characterized in that saccharose is used as the disaccharide.

10. The stable, injectable solution according to claim 4, characterized in that saccharose is used as the disaccharide.

11. The stable, injectable solution according to claim 1, characterized in that saccharose is contained in a concentration of from 0.4 to 0.65 mol/l.

12. The stable, injectable solution according to claim 2, characterized in that saccharose is contained in a concentration of from 0.4 to 0.65 mol/l.

13. The stable, injectable solution according to claim 3, characterized in that saccharose is contained in a concentration of from 0.4 to 0.65 mol/l.

14. The stable, injectable solution according to claim 4, characterized in that saccharose is contained in a concentration of from 0.4 to 0.65 mol/l.

* * * * *